(12) United States Patent
Salky

(10) Patent No.: US 8,591,530 B2
(45) Date of Patent: Nov. 26, 2013

(54) SUTURE GUIDE CLIP AND LAPAROSCOPIC TECHNIQUES

(75) Inventor: Barry A. Salky, New York, NY (US)

(73) Assignee: Cook Medical Technologies LLC, Bloomington, IN (US)

( * ) Notice: Subject to any disclaimer, the term of this patent is extended or adjusted under 35 U.S.C. 154(b) by 727 days.

(21) Appl. No.: 12/351,399

(22) Filed: Jan. 9, 2009

(65) Prior Publication Data

US 2010/0179569 A1 Jul. 15, 2010

(51) Int. Cl.
 *A61B 17/04* (2006.01)
(52) U.S. Cl.
 USPC .......................................... 606/148
(58) Field of Classification Search
 USPC ........................... 606/151, 153, 156, 157, 148
 See application file for complete search history.

(56) References Cited

U.S. PATENT DOCUMENTS

| | | | |
|---|---|---|---|
| 475,259 A | 5/1892 | Turck | |
| 669,034 A * | 2/1901 | Manly | 606/118 |
| 963,899 A * | 7/1910 | Kistler | 606/157 |
| 1,139,627 A | 5/1915 | Baltzley | |
| 1,865,453 A | 7/1932 | Baltzley | |
| 3,604,425 A | 9/1971 | LeRoy | |
| 4,332,060 A | 6/1982 | Sato | |
| 4,440,170 A * | 4/1984 | Golden et al. | 606/142 |
| 5,330,486 A | 7/1994 | Wilk | |
| 5,534,008 A * | 7/1996 | Acksel | 606/148 |
| 5,725,537 A | 3/1998 | Green et al. | |
| 5,896,624 A | 4/1999 | Horswell | |
| 7,305,741 B2 | 12/2007 | Joe | |

* cited by examiner

*Primary Examiner* — Gregory Anderson
(74) *Attorney, Agent, or Firm* — Brinks Gilson & Lione

(57) ABSTRACT

An anastomosis clip comprising a first side including a first end portion and at least one first suture guide, the first suture guide being disposed on a top of the clip, the first end portion and the first suture guide defining a first suture space open toward the top of the clip, the first side further including a first carrier slot on the bottom of the clip. The clip further includes a second-side, including a second end portion and at least one second suture guide, the second suture guide being disposed on the top of the clip, the second end portion and the second suture guide defining a second suture space open toward the top of the clip, the second side further including a second carrier slot on the bottom of the clip. The clip further includes a hinge connecting the first and second side, the hinge being disposed on the top of the clip. The first side is biased toward the second side. An introducer device including handles and posts may be used to introduce the anastomosis clip into a patient. In use, the posts on the introducer device are inserted into the suture guides. Thereafter, the clip is inserted into a patient and placed on two organ segments. The suture spaces allow for continuous suturing of the organ segments. As the sutures spaces may communicate with each other, the anastomosis clip may be removed from the organ segments after the suturing.

26 Claims, 11 Drawing Sheets

100

SUTURE GUIDE CLIP AND LAPAROSCOPIC TECHNIQUES

BACKGROUND OF THE INVENTION

Field of the Invention

This disclosure relates to laparoscopic anastomosis tools and techniques and, more particularly, to anastomosis tools and techniques that facilitate suturing.

An example of a prior art laparoscopic anastomosis technique 50 is described in U.S. Pat. No. 5,330,486—and is explained with reference to FIG. 1. In the shown technique, two organ segments 52, 54 are placed side-by-side and joined together. This joining may result in many benefits. For example, if a portion of the intestine is removed due to cancer, remaining portions of the intestine may be joined together using an anastomosis. In the example shown in FIG. 1, ends 56, 58 of the respective organ segments 52, 54, may be closed off. Connecting organ segment 52 with organ segment 54 may allow contents of organ segment 52 to flow through an opening 60 and into organ segment 54.

In order to perform the anastomosis technique, laparoscopic stapling members 62, 64 of respective laparoscopic stapling devices 66, 68, are inserted into organ segments 52, 54 via respective incisions or enterotomies 70, 72 formed in side walls of organ segments 52, 54. Laparoscopic stapling members 62, 64 are fixed to the ends of shafts 74, 76. The ends of shafts 74, 76 are adjustable by manipulating actuators 78, 80. Ends of shafts 74, 76 are inserted into a patient via respective trocar sleeves 82, 84 which traverse an abdominal wall 86.

Actuator 80 contains anastomosis staples and actuator 78 may contain an anvil member for assisting in the bending of the staple legs. A spindle 88 may be used to eject a threaded connector from actuator 80 into the anvil member. Actuator hand grips 90 are then squeezed to eject staples. Upon completion of the stapling operation, actuators 78, 80 are withdrawn from organ segments 52, 54 via enterotomies 70, 72. Enterotomies 70, 72 are then, in turn, closed.

Such prior art techniques have many problems. For example, by inserting stapling members 78, 80 through incisions 70, 72, additional suturing of incisors 70, 72 is necessitated. Moreover, these prior art techniques are limited to anastomosis using staples. However, stapling is not always the most desirable approach.

SUMMARY OF THE INVENTION

One embodiment of the invention is an anastomosis clip comprising a first side including a first end portion and at least one first suture guide, the first end portion and the first suture guide defining a first suture space open toward a top of the clip, the first side further including a first carrier slot on the bottom of the clip. The clip further includes a second side, including a second end portion and at least one second suture guide, the second end portion and the second suture guide defining a second suture space open toward the top of the clip, the second side further including a second carrier slot on the bottom of the clip. The clip further includes a hinge connecting the first and second side, the hinge being disposed on the top of the clip. The first side is biased toward the second side.

Another embodiment of the invention is a method for suturing two organ segments, the method comprises first manipulating an introducer device to open an anastomosis clip, inserting the introducer device and anastomosis clip into a patient, and placing the anastomosis clip over two organ segments. The method further comprises manipulating the introducer device to close the anastomosis clip on the two organ segments, suturing the organ segments using suture guides in the anastomosis clip and second manipulating the introducer device to open the anastomosis clip. The method further comprises lifting the introducer device and anastomosis clip off of the organ segments; and removing the introducer device and anastomosis clip from the patient.

Yet another embodiment of the invention is a combination of an anastomosis clip and an introducer device. The combination comprises an introducer device comprising a handle, and a first and a second post connected to the handle. The combination further comprises an anastomosis clip comprising a first side including a first end portion and at least one first suture guide, the first end portion and the first suture guide defining a first suture space open toward a top of the clip, the first side further including the first post on the bottom of the clip. The anastomosis clip further comprises a second side, including a second end portion and at least one second suture guide, the second end portion and the second suture guide defining a second suture space open toward the top of the clip, the second side further including the second post on the bottom of the clip. The anastomosis clip further comprises a hinge connecting the first and second side, the hinge being disposed on the top of the clip. The first side is biased toward the second side.

BRIEF DESCRIPTION OF THE DRAWINGS

The drawings constitute a part of the specification and include exemplary embodiments of the present invention and illustrate various objects and features thereof.

DETAILED DESCRIPTION OF THE PREFERRED EMBODIMENT(S)

Figure 1:
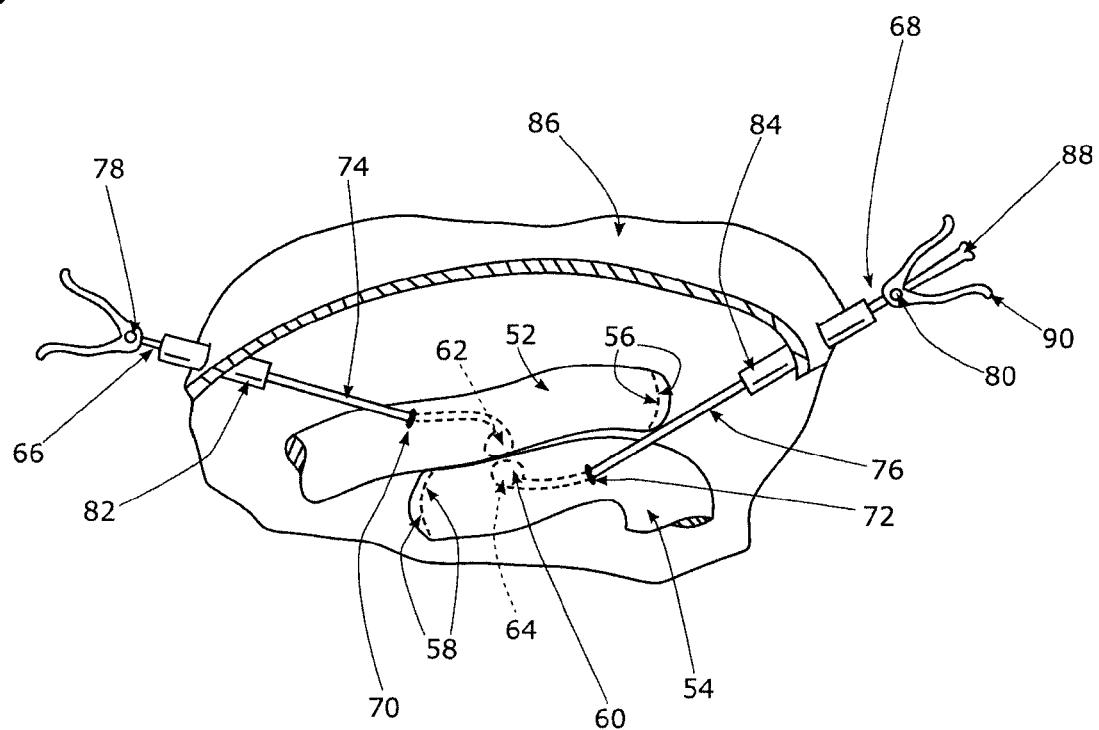
FIG. 1 is a front perspective cut-away view of an anastomosis technique in accordance with the prior art.

Various embodiments of the invention are described hereinafter with reference to the figures. Elements of like structures or function are represented with like reference numerals throughout the figures. The figures are only intended to facilitate the description of the invention or as a limitation on the scope of the invention. In addition, an aspect described in conjunction with a particular embodiment of the invention is not necessarily limited to that embodiment and can be practiced in conjunction with any other embodiments of the invention.

Figure 2:
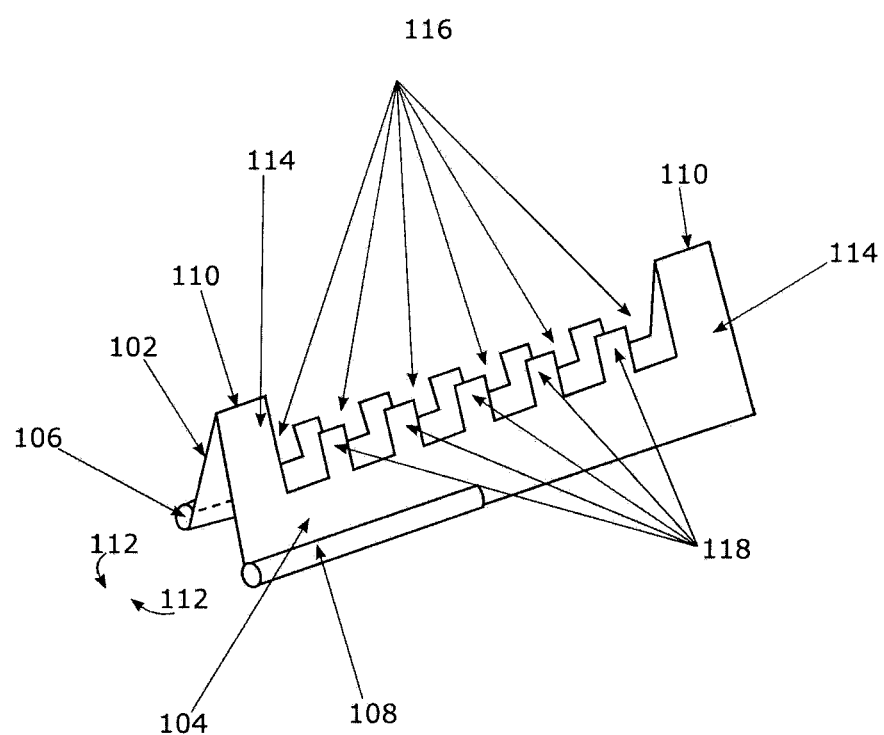
FIG. 2 is a perspective view of an anastomosis clip in accordance with an embodiment of the invention.

Referring now to FIG. 2, there is shown an anastomosis clip 100 in accordance with an embodiment of the invention. Clip 100 may be made of metal or plastic and could be made so as to be disposable. As seen in FIG. 2, clip 100 includes a first elongate side 102 connected to a second elongate side 104 by a hinge 110. First side 102 is biased closed toward second side 104 in the direction shown by direction arrows 112. Such a bias may be performed by a spring in hinge 110 or though the use of a material with a positional memory such as nitinol, though the use of a spring loaded plastic, by combining clip 100 with an introducer device (discussed below), or with any other known method or material. Sides 102, 104 include carrier slots 106, 108 respectively that may allow clip 100 to be used with an introducer device. Sides 102 and 104 are symmetrical, i.e., have the same shape and so a discussion of one side effectively includes a discussion of the other. Focusing on side 104, side 104 includes end portions 114 that terminate in hinges 110 and side 104 includes suture guides 118 both shown on a top of clip 100 though it should be clear that the terms top and bottom may be used interchangeably. End portions 114 and suture guides 118 define suture spaces 116 open toward the top of clip 100 and effective to allow for suturing of organ segments using clip 100. As seen in FIG. 2, the suture guides 118 have upwardly facing free ends and are situated one next to each other between the end portions 114. Each pair of adjacent suture guides 118 defines a suture space 116 between them which opens toward the top of the clip.

Figure 3:
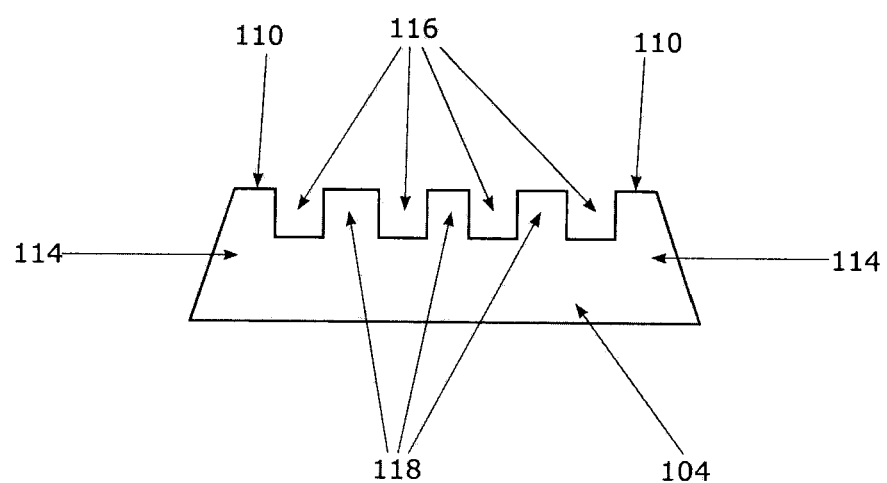
FIG. 3 is a side view of an anastomosis clip in accordance with an embodiment of the invention.
Figure 4:
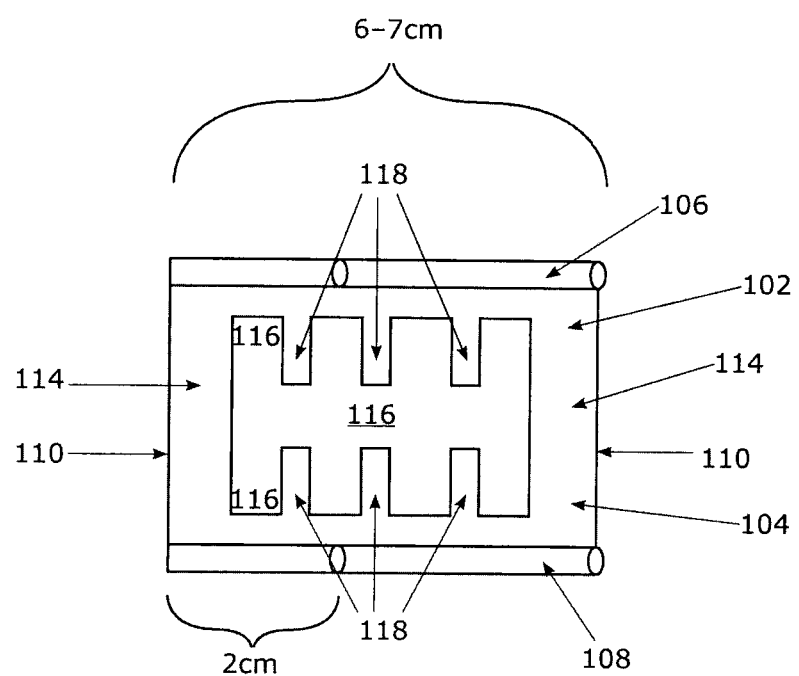
FIG. 4 is a top view of an open anastomosis clip in accordance with an embodiment of the invention.
Figure 5:
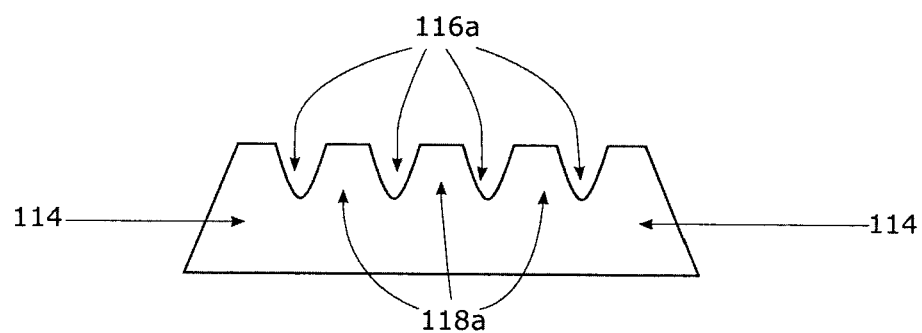
FIG. 5 is a side view of an anastomosis clip in accordance with an embodiment of the invention.

FIG. 2 shows five suture guides 118 though any number may be used. For example, as shown in FIG. 3, three suture guides 118 may be used. End portions 114 may taper outwardly. Suture guides 118 may have rectangular shapes as shown in FIGS. 2 and 3 and may extend inwardly as shown in FIG. 4 (where clip 100 is forced in an open position) to define suture spaces 116 having a fence shaped overall cross-section. As shown, sutures spaces 116 on first side 102 communicate with suture spaces 116 on second side 104 because suture guides 118 on first side 102 do not meet with, i.e., are separate and spaced from, suture guides 118 on second side 104. Some potential dimensions for clip 110 are also shown—an overall length of the clip 100 may be 6-7 cm where 2 cm of the clip excludes carrier slots 106, 108. Clip 100 may also include suture guides defining arcuate suture spaces as shown in FIG. 5 with suture guides 118a and arcuate suture spaces 116a. Clearly, any shape of suture guide may be used to define any type of suture space.

Figure 6:
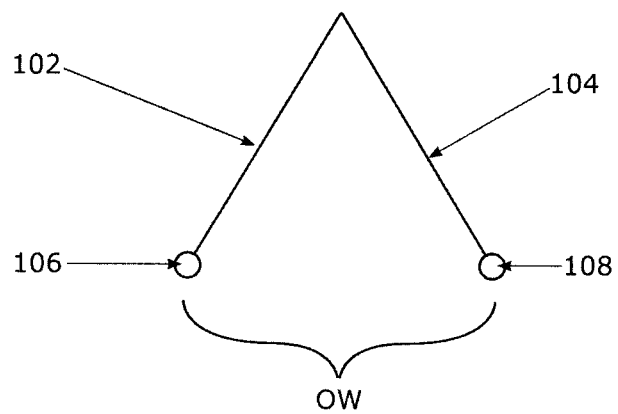
FIG. 6 is a front view of an open anastomosis clip in accordance with an embodiment of the invention.
Figure 7:
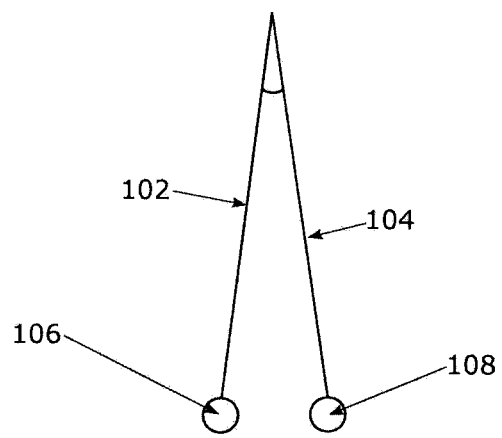
FIG. 7 is front view of a closed anastomosis clip in accordance with an embodiment of the invention.
Figure 8:
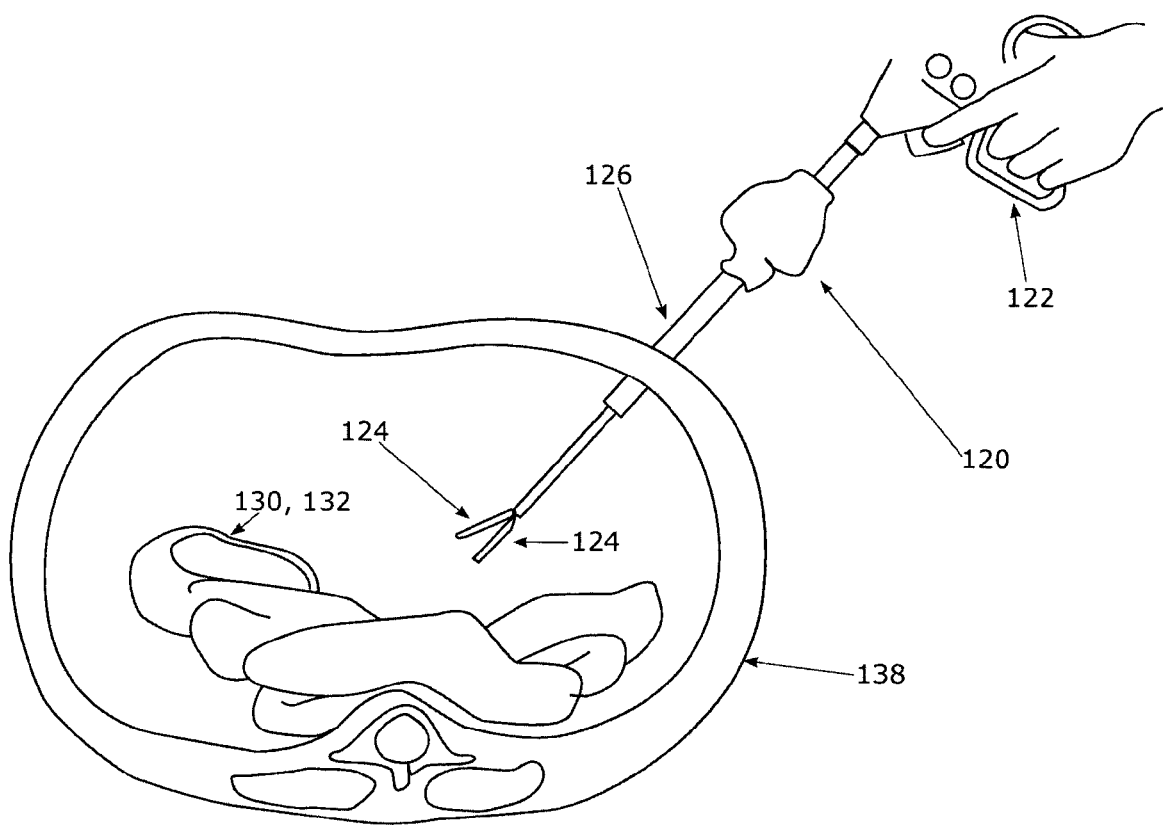
FIG. 8 is a side cut-away view of an introducer device inserted into a patient through a trocar in accordance with an embodiment of the invention.
Figure 9:
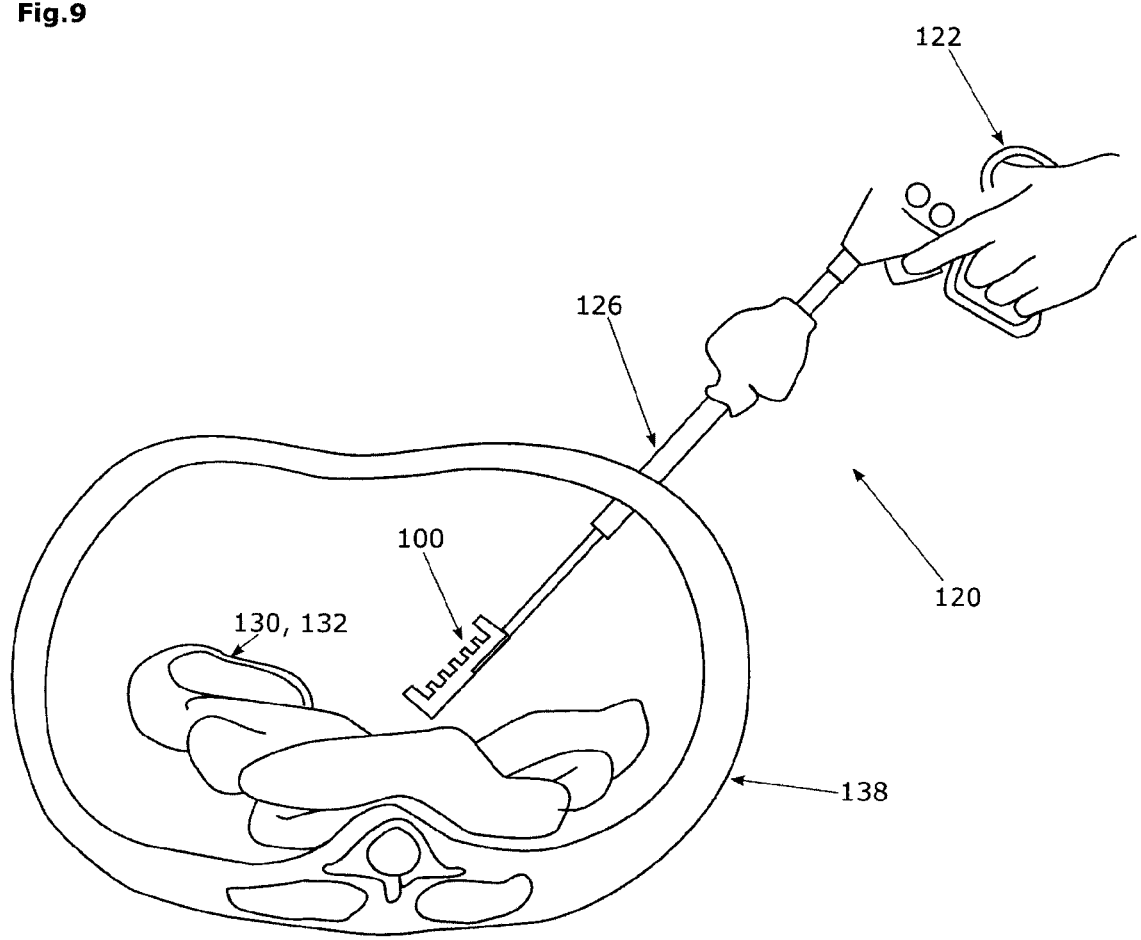
FIG. 9 is a side cut-away view of a combination of an introducer device and clip inserted into a patient through a trocar in accordance with an embodiment of the invention.

Clip 100 is biased toward a closed position. When clip 100 is used in an anastomosis procedure, clip 100 is first forced to an open position as shown in FIG. 6. Clip 100 may be used in a laparoscopic procedure using a trocar (FIGS. 8 and 9). As a consequence, clip 100 may be designed so that in the open position, carrier slots 106, 108 define an opening width OW that is not greater than 11 mm so as to fit in a 12 mm diameter trocar. Once clip 100 is in place around the organ segments, clip 100 is allowed to return to the closed position as shown in FIG. 7.

If clip 100 is used in a laparoscopic procedure, the patient may be prepared for such procedure in accordance with known techniques in the art. For example, one or more trocars (FIGS. 8 and 9) may be inserted into the patient and used, in conjunction with a fiber optic camera, to allow access of clip 100 inside the patient. FIGS. 8 and 9 show an introducer device 120 which could be used to introduce clip 100 through a trocar 126 into a patient 138 in a laparoscopic procedure. Introducer device 120 may be made of, for example plastic or metal. Introducer device 120 includes handles 122 and posts 124. Posts 124 may be inserted into carrier slots 106, 108 (FIG. 2) of clip 100 so that introducer device 120 can introduce clip 100 into a patient.

Manipulation of handles 122 together and apart causes movement of posts 124. For example, a squeezing of handles 122 toward one another may result in an opening or spreading apart of posts 124 as shown in FIG. 8. Conversely, a spreading of handles 122 may result in a closing of posts 124. Handles 122 and posts 124 may be naturally biased toward a position where posts 124 are closed, such as, for example, using a spring to bias handles 122 in an open position, through the use of nitinol, a spring biased plastic or any other known method.

For example, focusing on FIGS. 2, 8 and 9, as discussed above, clip 100 may be biased toward a closed position and posts 124 of introducer 120 may be biased toward a closed position. A user may insert posts 124 into carrier slots 106, 108. Alternatively, introducer 120 and clip 100 may be designed as a single instrument. The user may then squeeze handles 122 causing posts 124 and carrier slots 106, 108 to open (see FIGS. 6 and 8). As opening width OW (FIG. 6) of clip 100 may be 11 mm, introducer 120 and clip 100 may be inserted into a 12 mm diameter trocar 126 even while clip 100 is in an open position.

Figure 10:
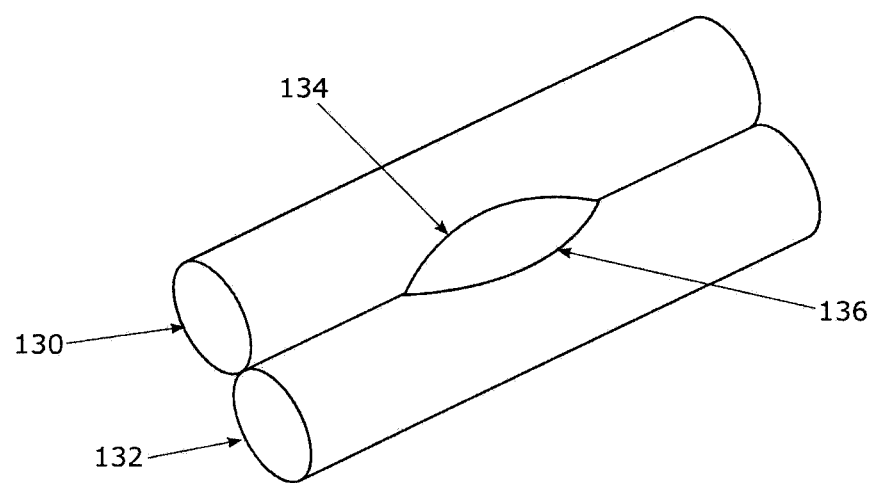
FIG. 10 is a front perspective view of two organ segments.
Figure 11:
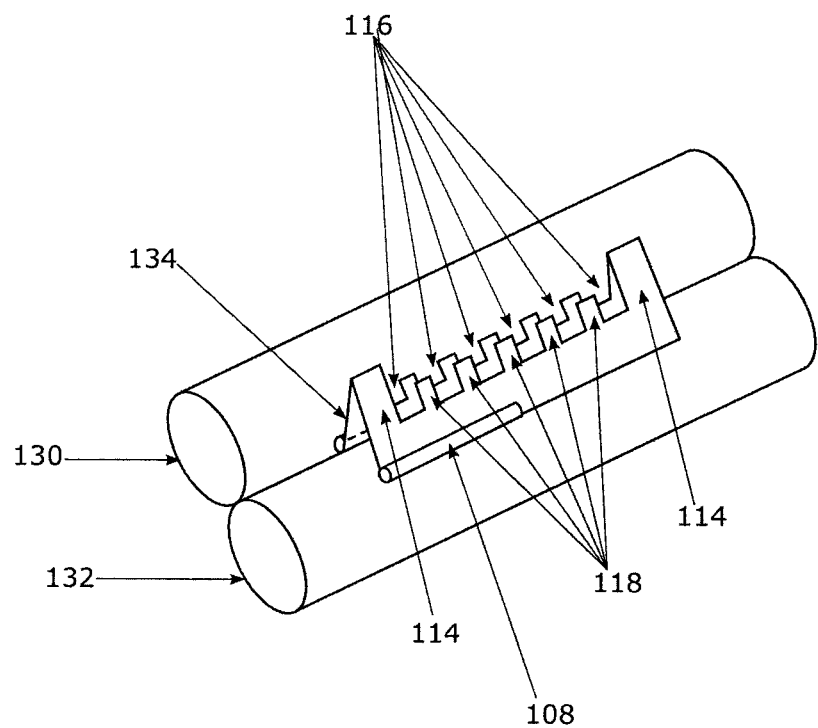
FIG. 11 is a front perspective view of two organ segments and an anastomosis clip in accordance with an embodiment of the invention.

FIG. 10 shows two organ segments 130, 132 placed side by side to one another. First and second sides 134, 136 of an opening are shown and it is desirable to suture sides 134, 136 together. Clip 100 may be used to facilitate such suturing. With posts 124 of introducer 120 forcing clip 100 open, clip 100 is placed over organ segments 130, 132 as shown in FIG. 11. Once clip 100 is in a desired position, a user may allow introducer 120 to close, thereby closing clip 100 on organ segments 130, 132 due to the bias of first side 102 toward seconds side 104. Introducer 120 may then be removed from the patient while clip 100 remains or an instrument comprised of a combination of an introducer device and clip may remain.

As discussed above, clip 100 includes suture spaces 116 defined by suture guides 118. Suture spaces 116 are designed to facilitate suturing or laparoscopic suturing. For example, clip 100 can line up organ segments 130, 132 so that a continuous suture can be applied. Prior art laparoscopic suturing is difficult because of, in part, the difficulties in lining up two ends of organ segments together to enable proper placement of needles for sutures. Clip 100 helps solve that problem by effectively lining up organ segments 130, 132, and holding organ segments 130, 132 next to one another while defining suture spaces 116 for suturing.

As shown in FIG. 11 and also in FIG. 4, as suture guides 118 on first side 102 do not meet with, i.e., are separate and spaced from, suture guides 118 on second side 104, a top of clip 100 is generally open because respective suture spaces 116 on sides 102, 104 communicate and both are open toward the top of clip 100. This means that sutures may be placed through suture spaces 116 and clip 100 may thereafter be lifted upward and removed from organ segments 130, 132. For example, after sutures (not shown) are used to suture opening 134, 136, if introducer 120 is separate from clip 100, introducer 120 may be reinserted into the patient and posts reinserted into carrier slots 106, 108. Handles 122 of introducer 120 are then squeezed to open posts 124, carrier slots 106, 108 and clip 100. Clip 100 may then be lifted off of organ segments 130, 132 and removed from a patient. Such a technique could be performed through a trocar or through traditional open surgery methods.

Unlike prior art devices and techniques, clip 100 allows for laparoscopic suturing of organ segments. Moreover, additional incisions are not needed for such suturing as is required in many prior art techniques resulting in less recuperation time and less pain for the patient. Further, the clip includes guides to facilitate the suturing—a difficult process if using prior art devices devoid of such guides.

The invention has been described with reference to an embodiment that illustrates the principles of the invention and is not meant to limit the scope of the invention. Modifications and alterations may occur to others upon reading and understanding the preceding detailed description. It is intended that the scope of the invention be construed as including all modifications and alterations that may occur to others upon reading and understanding the preceding detailed description insofar as they come within the scope of the following claims or equivalents thereof. Various changes may be made without departing from the spirit and scope of the invention.

What is claimed is:

1. An anastomosis clip comprising:
   a first side including a first end portion and at least one first suture guide, the first end portion and the first suture guide defining a first suture space open toward a top of the clip, the first side further including a first carrier slot on the bottom of the clip;
   a second side, including a second end portion and at least one second suture guide, the second end portion and the second suture guide defining a second suture space open toward the top of the clip, the second side further including a second carrier slot on the bottom of the clip;
   wherein the first suture space communicates with the second suture space; and
   a hinge connecting the first and second side, wherein the hinge biases the first side toward the second side, the hinge being disposed on the top of the clip.

2. The clip of claim 1, wherein the clip is configured to receive an organ segment to be sutured from a bottom of the clip.

3. The clip as recited in claim 1, wherein the first and second suture guides have a rectangular cross-section.

4. The clip as recited in claim 1, wherein the first and second suture spaces are arcuate.

5. The clip as recited in claim 1, wherein the first side, second side and hinge allow the first side to be opened from the second side by an opening width equal to or less than 11 mm.

6. The clip as recited in claim 1, wherein the first suture guide is distinct from the second suture guide.

7. The clip of claim 1 wherein
   the first side comprises a pair of first end portions and a plurality of adjacent first suture guides situated between the pair of first end portions, the plurality of first suture guides defining a plurality of first suture spaces between them; and
   the second side comprises a pair of second end portions and a plurality of adjacent second suture guides situated between the pair of second end portions, the plurality of second suture guides defining a plurality of second suture spaces between them.

8. A method for suturing two organ segments, the method comprising:
   manipulating an introducer device to open an anastomosis clip, the anastomosis clip comprising:
      a first side including a first end portion and at least one first suture guide, the first end portion and the first suture guide defining a first suture space open toward a top of the clip, the first side further including a first carrier slot on the bottom of the clip;
      a second side, including a second end portion and at least one second suture guide, the second end portion and the second suture guide defining a second suture space open toward the top of the clip, the second side further including a second carrier slot on the bottom of the clip;
      wherein the first suture space communicates with the second suture space; and
      a hinge connecting the first and second side, wherein the hinge biases the first side toward the second side, the hinge being disposed on the top of the clip;
   inserting the introducer device and anastomosis clip into a patient;
   placing the anastomosis clip over two organ segments;
   manipulating the introducer device to close the anastomosis clip on the two organ segments;
   suturing the organ segments using suture guides in the anastomosis clip;
   manipulating the introducer device to re-open the anastomosis clip;
   removing the introducer device and anastomosis clip from the organ segments; and
   removing the introducer device and anastomosis clip from the patient.

9. The method as recited in claim 8, further comprising:
   inserting posts of the introducer device into carrier slots of the anastomosis clip before the step of manipulating the introducer device,
   removing the introducer device from the patient before the step of suturing; and
   after the suturing, inserting the posts of the introducer device into the carrier slots of the anastomosis clip.

10. The method as recited in claim 8, wherein the inserting the introducer device, suturing, and removing the introducer device are performed through a trocar.

11. The method as recited in claim 8, wherein the first and second suture guides have a rectangular cross-section.

12. The method as recited in claim 8, wherein the first and second suture spaces are arcuate.

13. The method as recited in claim 8, wherein the first side, second side and hinge allow the first side to be opened from the second side by an opening width equal to or less than 11 mm.

14. The method as recited in claim 8, wherein the first suture space is distinct from the second suture space.

15. The method as recited in claim 8, wherein the first suture space communicates with the second suture space.

16. The method as recited in claim 8, wherein the introducer device biases the first side toward the second side.

17. A combination of an anastomosis clip and an introducer device, the combination comprising:
   an introducer device and an anastomosis clip;
   the introducer device comprising:
      a handle, and
      a first and a second post connected to the handle; and
   the anastomosis clip comprising:
      a first side including a first end portion and at least one first suture guide, the first end portion and the first suture guide defining a first suture space open toward a top of the clip;
      a second side, including a second end portion and at least one second suture guide, the second end portion and the second suture guide defining a second suture space open toward the top of the clip;
      wherein the first suture space communicates with the second suture space; and
      a hinge connecting the first and second side, wherein the hinge biases the first side toward the second side, the hinge being disposed on the top of the clip.

18. The combination as recited in claim 17, wherein: the first side of the clip includes a first carrier slot on the bottom of the clip; the second side of the clip includes a second carrier slot on the bottom of the clip; and the first and second posts of the introducer device are disposed in the first and second carrier slots.

19. The combination as recited in claim 17, wherein the first and second suture guides have a rectangular cross-section.

20. The combination as recited in claim 17, wherein the first and second suture spaces are arcuate.

21. The combination as recited in claim 17, wherein the first side, second side and hinge allow the first side to be opened from the second side by an opening width equal to or less than 11 mm.

22. The combination as recited in claim 17, wherein the first suture guide is distinct from the second suture guide.

23. The combination as recited in claim 17, wherein the first suture space communicates with the second suture space.

24. The combination as recited in claim 17, wherein the first and second posts are biased toward an open position.

25. The combination as recited in claim 17, wherein the introducer device biases the first side toward the second side.

26. The combination as recited in claim 17 wherein the clip is configured to receive an organ segment to be sutured from a bottom of the clip.

* * * * *